(12) United States Patent
Nakadate et al.

(10) Patent No.: US 10,702,352 B2
(45) Date of Patent: Jul. 7, 2020

(54) BENDING TREATMENT INSTRUMENT OPERATING PORTION

(71) Applicants: Kyushu University, National University Corporation, Fukuoka-shi, Fukuoka (JP); HOGY MEDICAL CO., LTD., Tokyo (JP)

(72) Inventors: Ryu Nakadate, Fukuoka (JP); Hajime Kenmotsu, Fukuoka (JP); Makoto Hashizume, Fukuoka (JP); Hiroyasu Fujita, Tokyo (JP); Shunsuke Nagai, Tokyo (JP); Jiro Kato, Tokyo (JP)

(73) Assignees: Kyushu University, National University Corporation, Fukuoka-shi, Fukuoka (JP); HOGY MEDICAL CO., LTD., Minato-ku, Tokyo (JP)

( * ) Notice: Subject to any disclaimer, the term of this patent is extended or adjusted under 35 U.S.C. 154(b) by 282 days.

(21) Appl. No.: 15/564,597

(22) PCT Filed: Apr. 15, 2015

(86) PCT No.: PCT/JP2015/061563
§ 371 (c)(1),
(2) Date: Oct. 5, 2017

(87) PCT Pub. No.: WO2016/166828
PCT Pub. Date: Oct. 20, 2016

(65) Prior Publication Data
US 2018/0078323 A1 Mar. 22, 2018

(51) Int. Cl.
*A61B 34/00* (2016.01)
*A61B 17/29* (2006.01)
(Continued)

(52) U.S. Cl.
CPC ............ *A61B 34/71* (2016.02); *A61B 17/29* (2013.01); *A61B 17/295* (2013.01);
(Continued)

(58) Field of Classification Search
CPC ............ A61B 17/00234; A61B 17/29; A61B 2017/003; A61B 2017/00305;
(Continued)

(56) References Cited

U.S. PATENT DOCUMENTS 5,454,827 A 10/1995 Aust et al.
2007/0021737 A1 1/2007 Lee
(Continued)

FOREIGN PATENT DOCUMENTS

JP 2007-319661 A 12/2007
JP 2009-505688 A 2/2009
JP 2010-511440 A 4/2010

OTHER PUBLICATIONS

International Search Report for PCT/JP2015/061563 dated Jun. 2, 2015.

*Primary Examiner* — Melanie R Tyson
(74) *Attorney, Agent, or Firm* — Sughrue Mion, PLLC

(57) ABSTRACT

An operating portion which allows a bending treatment instrument to be inserted into an endoscope channel and bendably operated smoothly through intuition. The operating portion is connected with a device wire and bending wires and used to operate the treatment instrument and bend a freely bendable, bending treatment instrument, where the device wire is connected to a treatment instrument provided at a distal end of the bending treatment instrument and is used to operate the treatment instrument and the plurality of bending wires is used to bend the bending treatment instrument, the operating portion including: an operating portion body; a guide unit penetrated by the device wire; a bending
(Continued)

wire pulling unit connected with the bending wires and swingably assembled onto the guide unit; and a grip portion connected with the device wire and configured to be reciprocable in an axial direction of the bending wire pulling unit.

8 Claims, 12 Drawing Sheets

(51) Int. Cl.
  *A61B 17/295* (2006.01)
  *A61B 17/00* (2006.01)
  *A61B 90/50* (2016.01)

(52) U.S. Cl.
  CPC .......... *A61B 17/2909* (2013.01); *A61B 34/74* (2016.02); *A61B 90/50* (2016.02); *A61B 2017/0034* (2013.01); *A61B 2017/00269* (2013.01); *A61B 2017/00323* (2013.01); *A61B 2017/00438* (2013.01); *A61B 2017/00991* (2013.01); *A61B 2017/291* (2013.01); *A61B 2017/2906* (2013.01); *A61B 2017/2929* (2013.01)

(58) Field of Classification Search
  CPC  A61B 2017/00318; A61B 2017/00323; A61B 2017/0034; A61B 34/35; A61B 34/70; A61B 34/71; A61B 34/74; A61B 2034/301; A61B 2034/303; A61B 2034/304; A61B 2034/715
  See application file for complete search history.

(56) References Cited

U.S. PATENT DOCUMENTS

| | | |
|---|---|---|
| 2007/0250110 A1 | 10/2007 | Lu et al. |
| 2009/0054734 A1* | 2/2009 | DeSantis ............... A61B 1/008 600/153 |
| 2011/0152609 A1* | 6/2011 | Trusty ............... A61B 1/00149 600/102 |
| 2012/0118088 A1 | 5/2012 | Smith et al. |
| 2015/0045620 A1 | 2/2015 | Kwon |

* cited by examiner

BENDING TREATMENT INSTRUMENT OPERATING PORTION

CROSS REFERENCE TO RELATED APPLICATIONS

This application is a National Stage of International Application No. PCT/JP2015/061563 filed Apr. 15, 2015, the contents of all of which are incorporated herein by reference in their entirety.

TECHNICAL FIELD

The present invention relates to an operating portion used to operate a bendable, bending treatment instrument inserted into a flexible endoscope, and specifically, to a bending treatment instrument equipped with a bending treatment instrument operating portion which allows a distal end of a treatment instrument such as a scalpel or forceps used to resect cancer such as epithelial cancer to be freely bent independently of the flexible endoscope by inserting the treatment instrument into a treatment instrument channel of the flexible endoscope or into a treatment instrument passage tube attached to the flexible endoscope and taking the treatment instrument to the digestive tract such as the stomach or intestines through the mouth or anus together with the flexible endoscope.

BACKGROUND ART

In recent years, operative procedures such as endoscopic submucosal dissection (ESD) have come to be used, where ESD involves inserting a treatment instrument through the mouth or anus and removing one slice from an upper layer of a mucous membrane over a wide area of the stomach or large intestine without penetrating stomach or large-intestine walls. Furthermore, an operative procedure (NOTES: Natural Orifice Translumenal Endoscopic Surgery) is known which involves inserting a flexible endoscope such as an upper or lower gastrointestinal endoscope through the mouth, anus, vagina, or urethra which originally exists in the surface of the body, then taking the flexible endoscope to an abdominal cavity by penetrating a stomach or large-intestine wall, and conducting diagnosis or treatment on an abdominal organ.

Since the natural orifice translumenal endoscopic surgery typified by endoscopic submucosal dissection (ESD) conducts treatment or the like by inserting a treatment instrument such as forceps or a scalpel together with a flexible endoscope through the mouth or the like which originally exists in the surface of the body, and taking the treatment instrument to a diseased part, the surgery causes no damage to the surface of the body, can eliminate complications such as infection or adhesion of the abdominal wall, which accompany ordinary surgery, and can reduce stress on the human body.

As described in Patent Literature 1, the treatment instrument used for the natural orifice translumenal endoscopic surgery includes a bending portion inserted into the flexible endoscope and used to bendably manipulate the treatment instrument projecting from a distal end of the flexible endoscope. Also, the treatment instrument includes a sheath and wire unit adapted to transmit bending motion to the bending portion and an operating portion used to manipulate the bending motion of the bending portion by pushing and pulling the sheath and wire.

Also, regarding a configuration of the operating portion, a structure is known in which a control member having at least two degrees of freedom is attached to a rail and multiple degrees of freedom are given to a treatment instrument.

CITATION LIST

Patent Literature

Patent Literature 1: Japanese Patent Laid-Open No. 2010-511440

SUMMARY OF INVENTION

Technical Problem

However, the bending treatment instrument described in Patent Literature 1 has an outside diameter of approximately 4.0 mm, which is a size not suitable for passage through an endoscope channel of the endoscope. Thus, the bending treatment instrument cannot to be taken safely to the stomach or the like from the mouth through the esophagus and is practically unusable. On the other hand, any attempt to reduce the outside diameter to such a size as to enable insertion into the endoscope channel to allow application to the above-mentioned endoscopic submucosal dissection (ESD) will obstruct bendability of the treatment instrument as well as appropriate grasping with forceps and resection with a scalpel, and consequently appropriate reduction of the diameter has not yet been achieved.

Furthermore, when the treatment instrument described in Patent Literature 1 is inserted into the endoscope channel of the flexible endoscope, the treatment instrument, bending portion, and sheath and wire unit may become twisted due to friction in the endoscope channel and the like. If the operating portion is operated in the twisted state, there is a problem in that a discrepancy occurs between a bending direction of the bending portion and an input direction of the operating portion, disabling intuitive operation.

Also, although various shapes are known concerning the endoscope channel of the flexible endoscope, including those with diameter sizes of about 3.8 mm, 3.2 mm, and 2.8 mm, any of the shapes is small in diameter, and when a bending treatment instrument is used by being inserted into the endoscope channel, spacing between the sheath and wire used to insert the bending treatment instrument into such a small diameter is reduced, which poses a problem in that manipulation of the operating portion increases friction between the sheath and wire, disabling transmission of a force applied through the operating portion to the bending portion and treatment instrument.

The present invention has been made to solve the above problems and specifically has an object to provide an operating portion which allows a bending treatment instrument to be inserted into an endoscope channel and bendably operated smoothly through intuition.

Solution to Problem

To solve the above problem, the present invention provides an operating portion connected with a device wire and a plurality of bending wires and used to operate a treatment instrument and bend a freely bendable, bending treatment instrument, the device wire being connected to the treatment instrument provided at a distal end of the bending treatment instrument and used to operate the treatment instrument and the plurality of bending wires being used to bend the bending treatment instrument, the operating portion comprising: an operating portion body; a guide unit penetrated by the device wire; a bending wire pulling unit connected with the bending wires and swingably assembled onto the guide unit; and a grip portion connected with the device wire and configured to be reciprocable in an axial direction of the bending wire pulling unit.

Also, in the operating portion according to the present invention, preferably the bending wire pulling unit and the guide unit include an axis alignment mechanism made up of a spherical recess and a spherical projection fitted one inside another, the spherical recess being formed in one of the bending wire pulling unit and the guide unit, and the spherical projection being formed on another of the bending wire pulling unit and the guide unit.

Also, in the operating portion according to the present invention, preferably the operating portion body is detachably attached to a fixing base via a fixing base connecting portion.

Also, in the operating portion according to the present invention, preferably a rotating device adapted to rotatably assemble the operating portion body onto the fixing base connecting portion is attached to the operating portion body, and the rotating device includes a fixing unit fixed to the fixing base connecting portion.

Also, in the operating portion according to the present invention, preferably the fixing base connecting portion includes a holding device adapted to hold the operating portion body in a longitudinal direction.

Also, in the operating portion according to the present invention, preferably the fixing base connecting portion includes a linear-motion device adapted to guide the operating portion body in an extending direction of the device wire.

Also, in the operating portion according to the present invention, preferably the operating portion body includes a twisting force relief mechanism adapted to prevent twisting of the device wire and the bending wires in a circumferential direction.

Also, in the operating portion according to the present invention, preferably the twisting force relief mechanism includes: a twisting force relief mechanism body adapted to allow passage of the device wire and the bending wires; and a rotating body assembled immovably relative to the twisting force relief mechanism body in a passage direction of the device wire and the bending wires and turnably in the circumferential direction.

Also, in the operating portion according to the present invention, preferably the fixing base connecting portion includes a holding device adapted to anchor, through press-fitting, a cover body attached to the operating portion body.

Also, in the operating portion according to the present invention, preferably the holding device includes a first anchoring portion and a second anchoring portion both shaped like a groove and configured to extend substantially at right angles to a longitudinal direction.

ADVANTAGEOUS EFFECTS OF INVENTION

According to the present invention, since the operating portion comprises an operating portion body; a guide unit penetrated by the device wire; a bending wire pulling unit connected with the bending wires and swingably assembled onto the guide unit; and a grip portion connected with the device wire and configured to be reciprocable in an axial direction of the bending wire pulling unit, the bending wire pulling unit can be operated in a manner similar to a joystick, making it possible to implement intuitive operation.

Also, according to the present invention, since the bending wire pulling unit and the guide unit include an axis alignment mechanism made up of a spherical recess and a spherical projection fitted one inside another, where the spherical recess is formed in one of the bending wire pulling unit and the guide unit while the spherical projection is formed on another of the bending wire pulling unit and the guide unit, the bending wire pulling unit can be operated in a manner similar to a joystick, and even if the bending wire pulling unit is tilted, the device wire can be pulled smoothly without causing displacement of a center axis of the device wire.

Also, according to the present invention, since the operating portion body is detachably attached to a fixing base via a fixing base connecting portion, intuitive one-hand operation can be implemented.

Also, according to the present invention, since a rotating device adapted to rotatably assemble the operating portion body onto the fixing base connecting portion is attached to the operating portion body, if a discrepancy occurs between a bending direction of the bending portion and an input direction of the operating portion due to twisting caused when the bending treatment instrument is inserted into the endoscope channel, by rotating the operating portion body via the rotating device, the input direction of the operating portion and the bending direction of the bending portion can be brought into coincidence with each other, making it possible to implement intuitive operation.

Also, according to the present invention, since the fixing base connecting portion includes a holding device adapted to hold the operating portion body in a longitudinal direction, the operating portion body is enabled to perform rotating motion and held securely, allowing the operating portion to be attached and detached easily to/from the fixing base.

Also, according to the present invention, since the fixing base connecting portion includes a linear-motion device adapted to guide the operating portion body in an extending direction of the device wire, a distal end position of the bending treatment instrument can be adjusted easily by pushing and pulling the bending treatment instrument itself.

Also, according to the present invention, since the operating portion body includes a twisting force relief mechanism adapted to prevent twisting of the device wire and the bending wires in a circumferential direction, even if a twisting force is applied to a sheath through which the device wire and bending wires are passed, the twisting force is scattered, and operation of the device wire and bending wires is not obstructed.

Also, according to the present invention, since the twisting force relief mechanism includes a twisting force relief mechanism body and a rotating body, the twisting force of the device wire and bending wires can be scattered using a simple structure.

Also, according to the present invention, since the fixing base connecting portion includes a holding device adapted to anchor, through press-fitting, a cover body attached to the operating portion body, the operating portion body can be fixed easily by simply press-fitting the cover body into the holding device.

Also, according to the present invention, since the holding device includes a first anchoring portion and a second anchoring portion both shaped like a groove and configured to extend substantially at right angles to a longitudinal direction, the operating portion body can be attached and detached easily.

BRIEF DESCRIPTION OF DRAWINGS

FIG. 4(a) is a configuration diagram illustrating a configuration of the sheath and wire unit, FIG. 4(b) is a diagram illustrating a variation of a bending wire and device wire, and FIG. 4(c) is a sectional view of the variation of the bending wire and device wire.

DESCRIPTION OF EMBODIMENTS

An operating portion according to the present invention and a bending treatment instrument with the operating portion assembled thereon will be described below with reference to the drawings. Note that the embodiments described below are not intended to limit the claimed invention and that a combination of all the features described in the embodiments are not necessarily essential for the means to solve the problems according to the present invention.

First Embodiment

Figure 1:
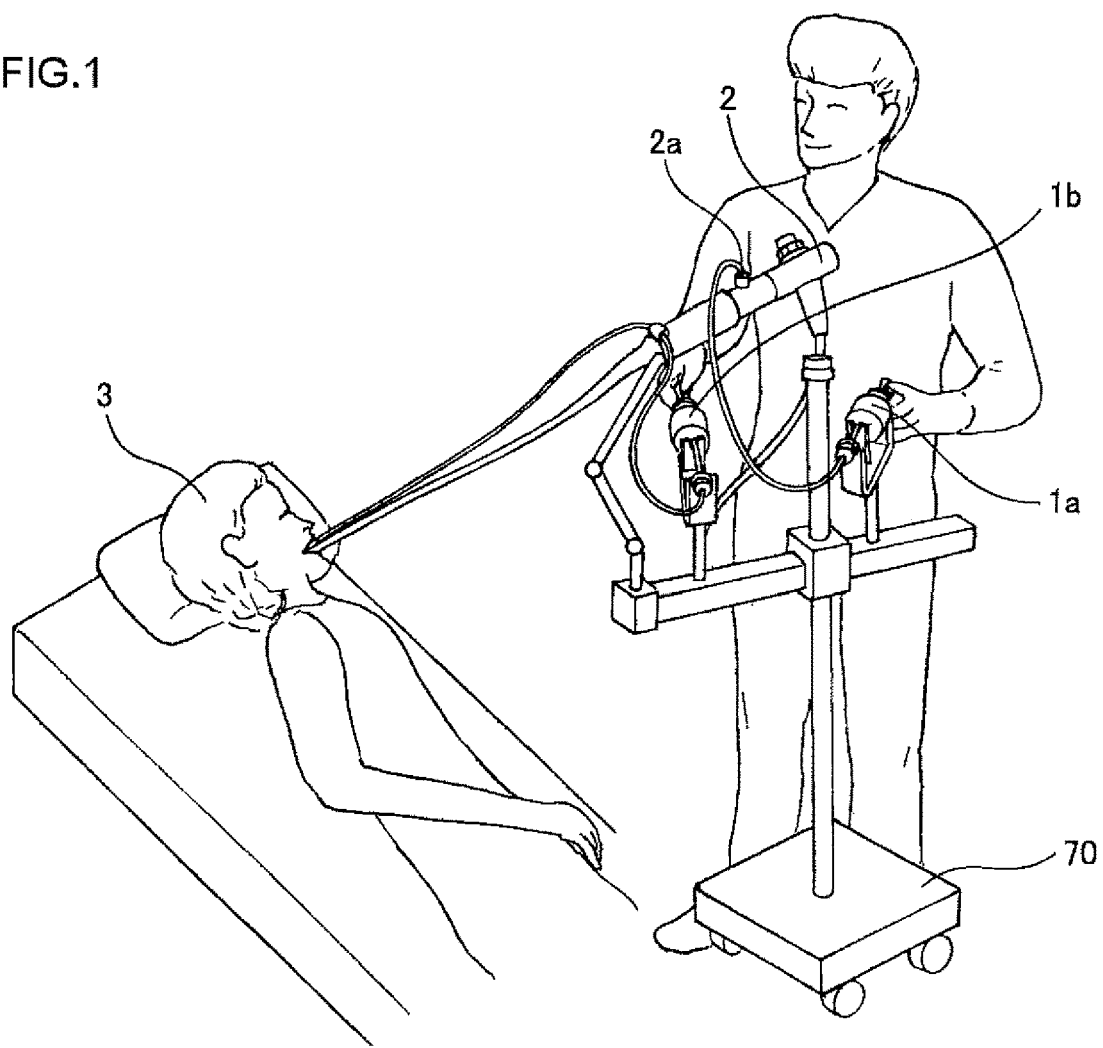
FIG. 1 is a schematic diagram illustrating how a bending treatment instrument according to a first embodiment is used.
Figure 2:
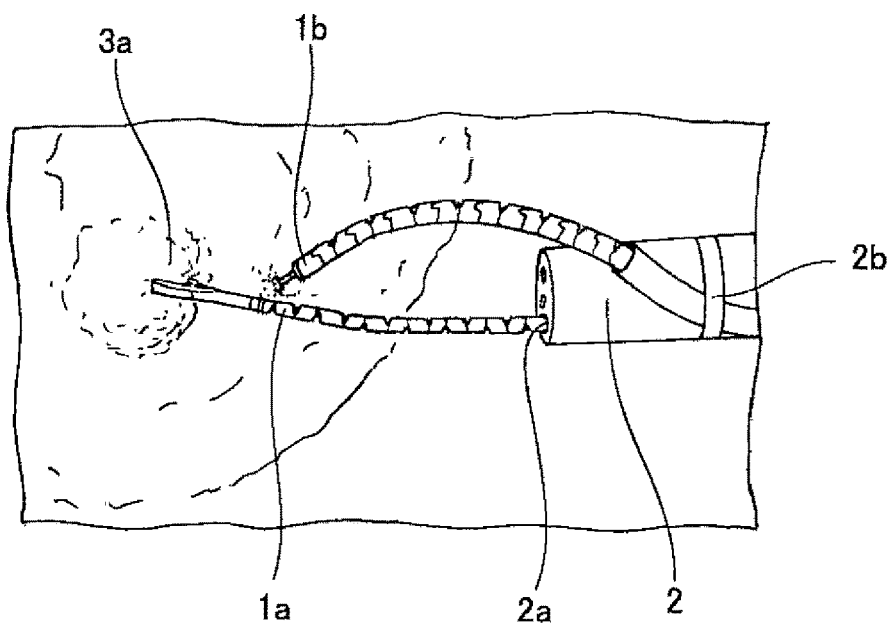
FIG. 2 is a schematic diagram illustrating an example of use of the bending treatment instrument according to the first embodiment.
Figure 3:
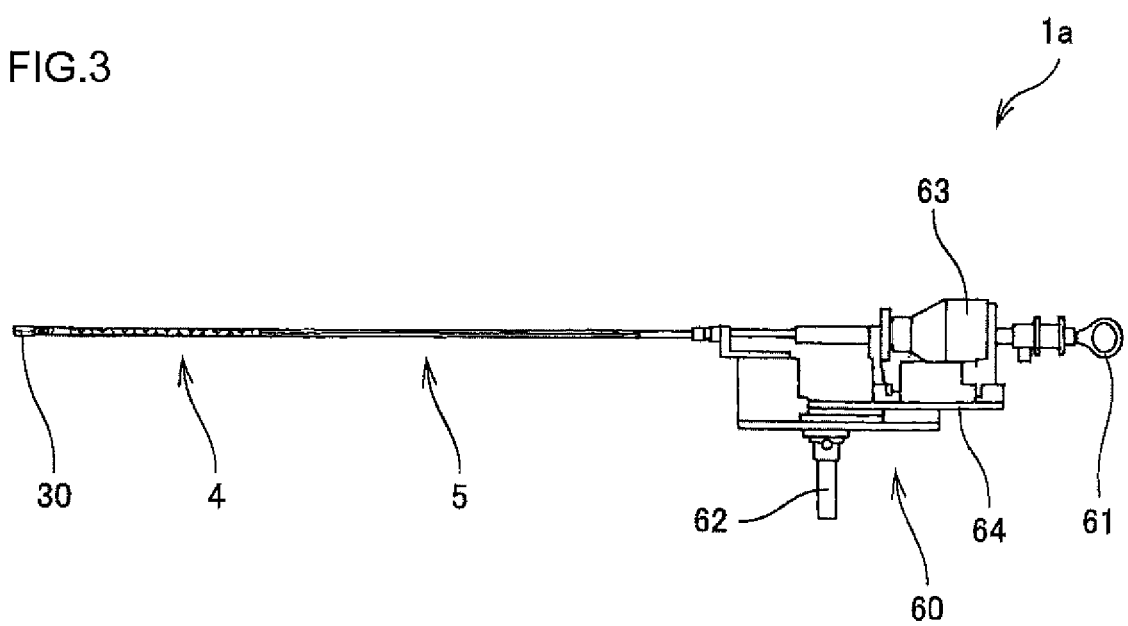
FIG. 3 is a side view illustrating a configuration of a forceps-equipped bending treatment instrument according to the first embodiment.
Figure 4A:
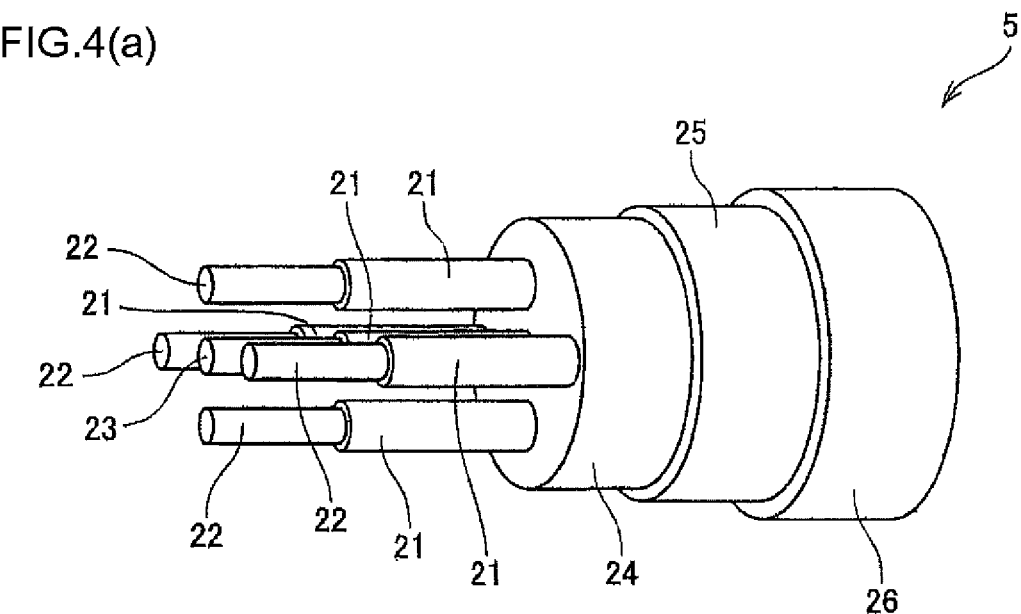
FIGS. 4(a) to 4(c) are configuration diagrams each illustrating a configuration of a sheath and wire unit, where
Figure 4B:
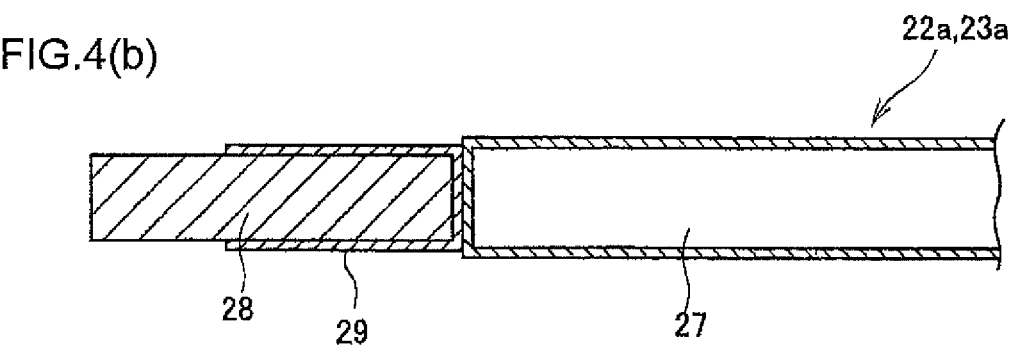
Figure 4C:
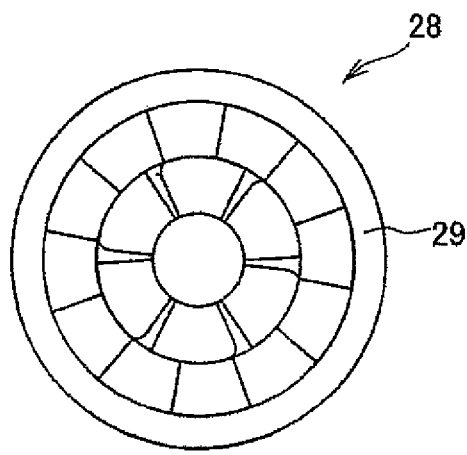
Figure 5:
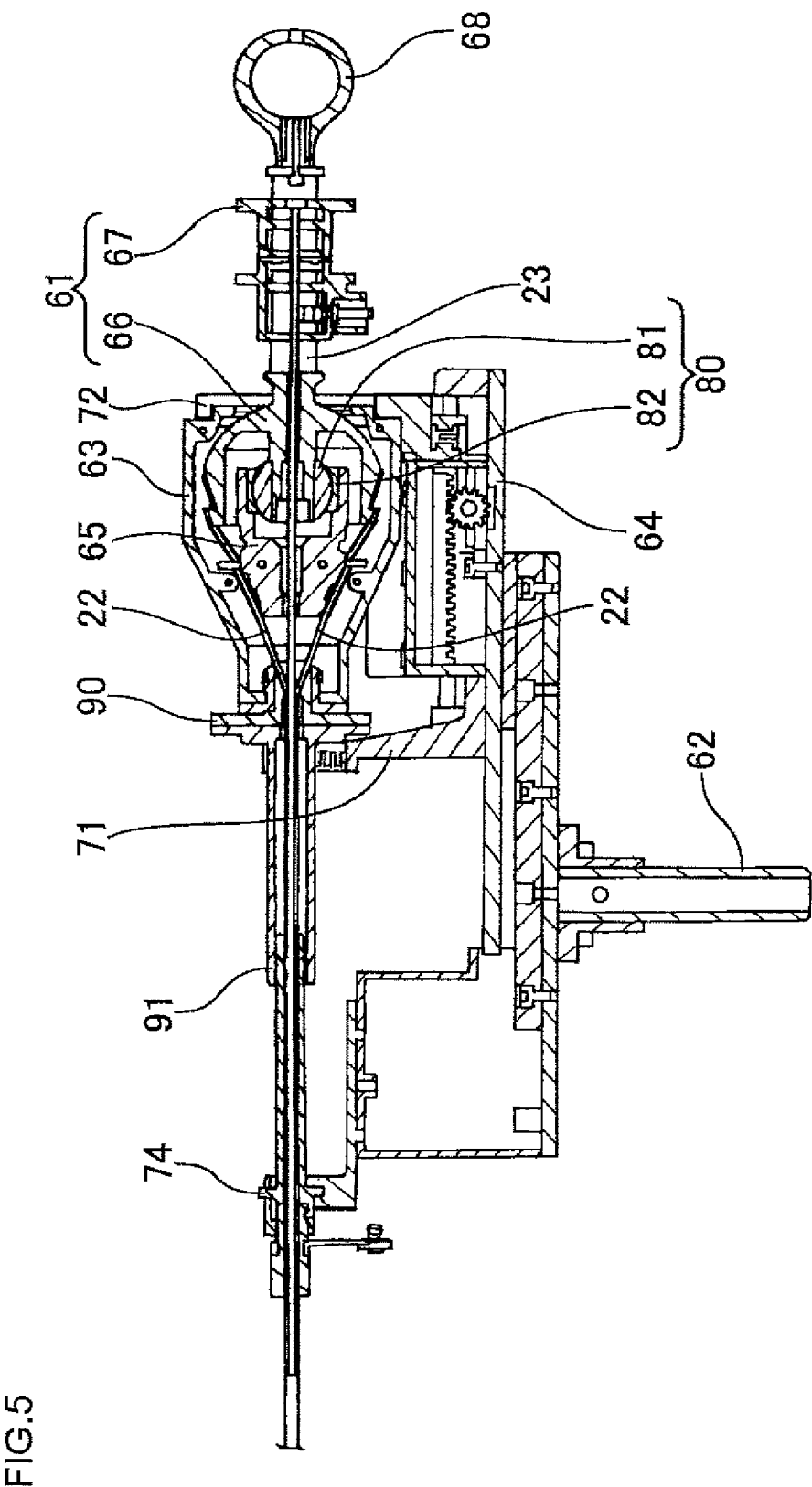
FIG. 5 is a sectional view of an operating portion of the bending treatment instrument according to the first embodiment.
Figure 6:
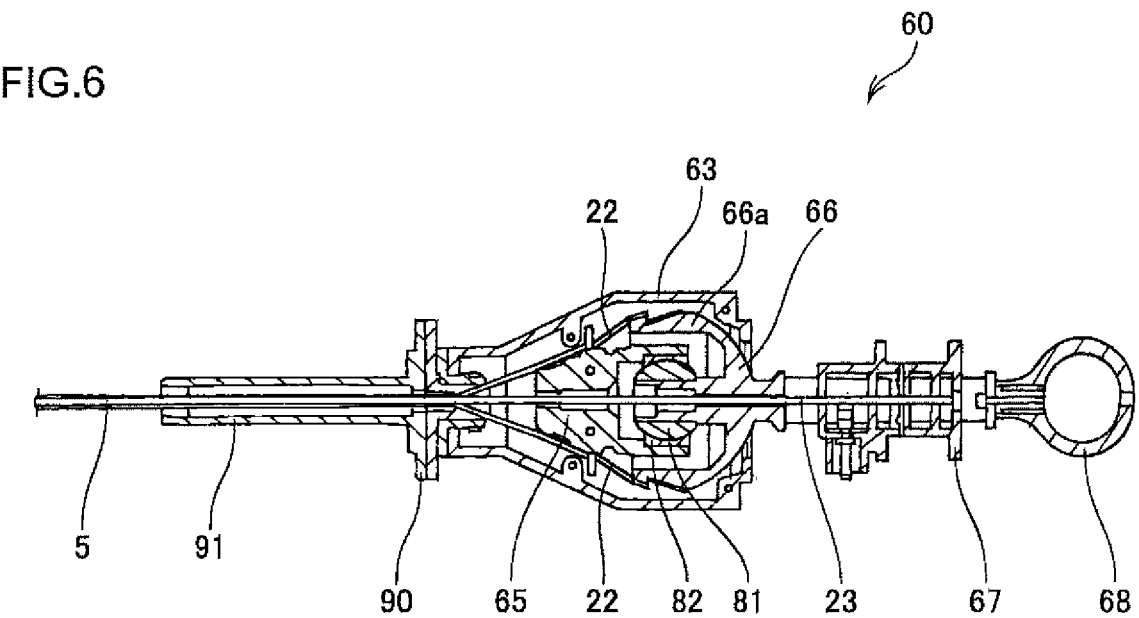
FIG. 6 is a sectional view illustrating an internal structure of the operating portion.
Figure 7:
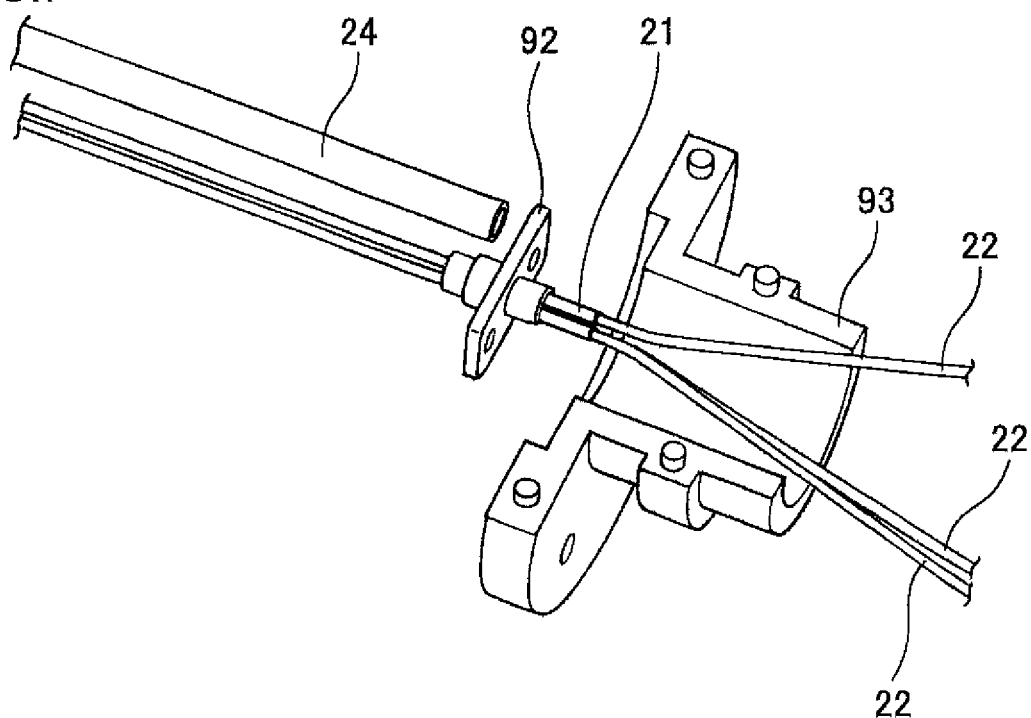
FIG. 7 is an exploded view illustrating a structure of a rotating device.
Figure 8:
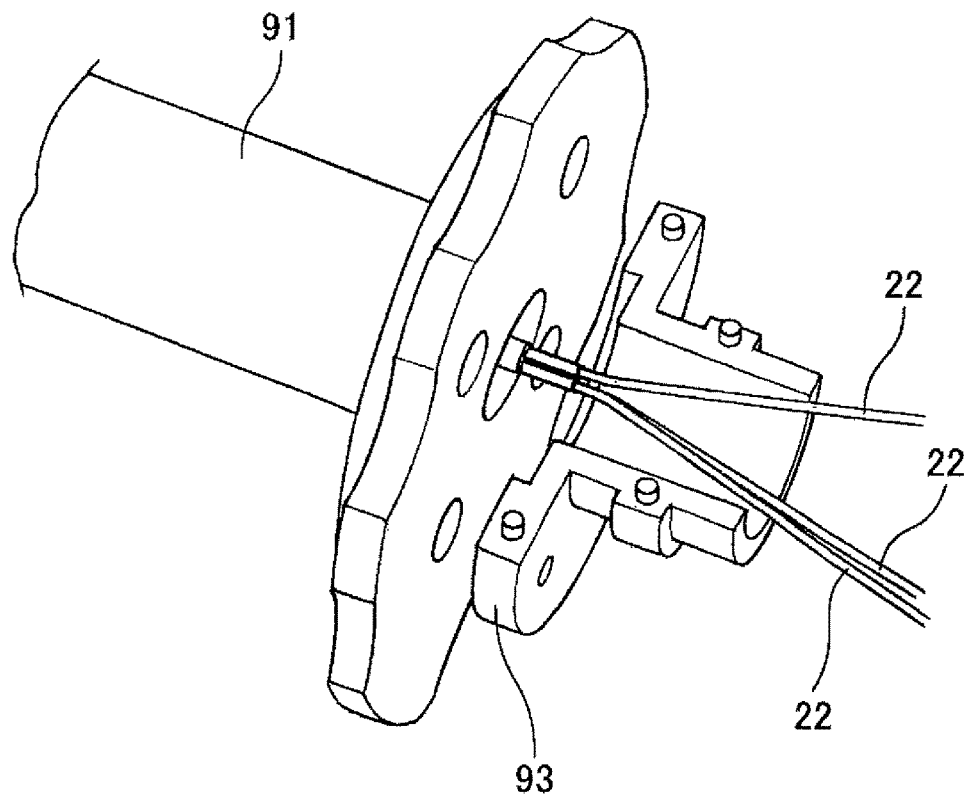
FIG. 8 is an exploded view illustrating a structure of the rotating device.
Figure 11:
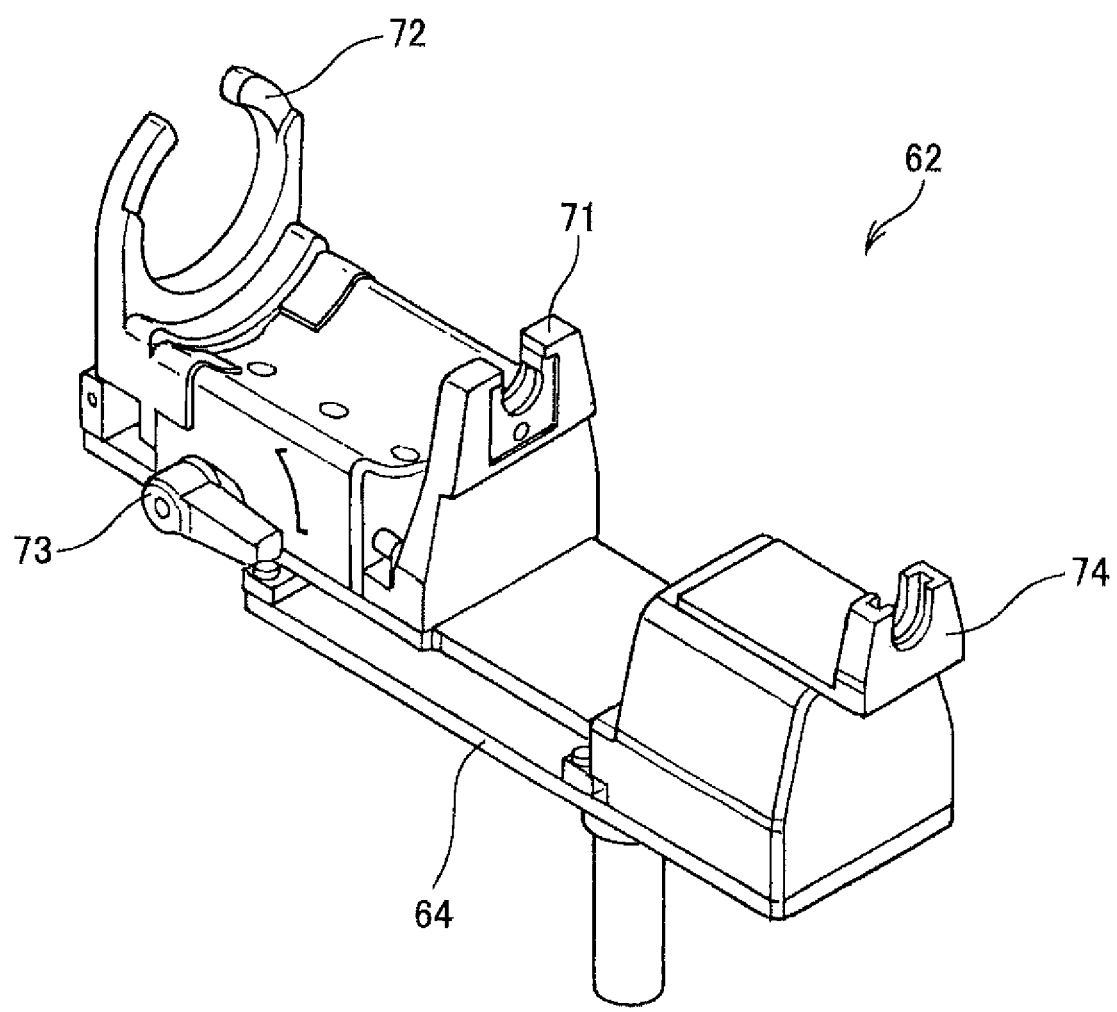
FIG. 11 is a perspective view of a fixing base connecting portion.
Figure 12:
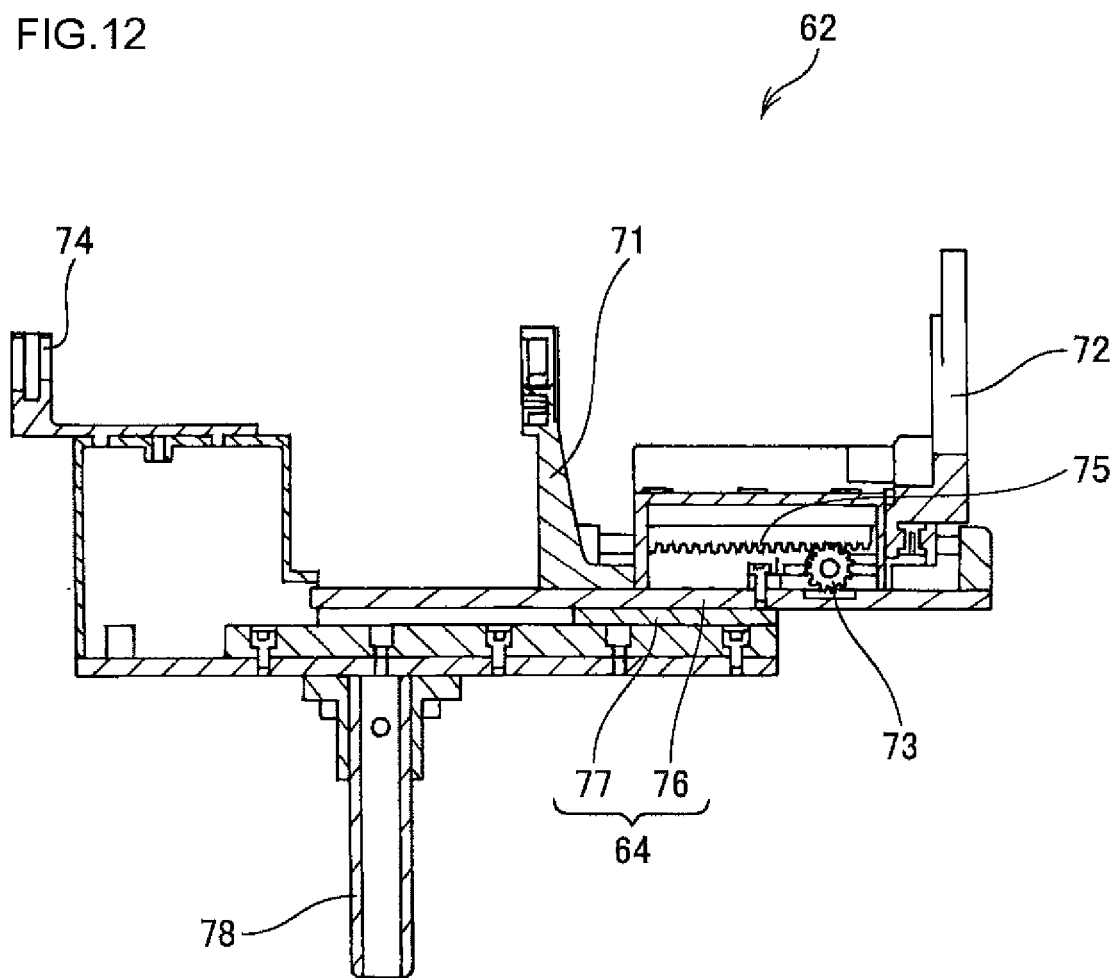
FIG. 12 is a sectional view illustrating an internal structure of the fixing base connecting portion.

FIG. 1 is a schematic diagram illustrating how a bending treatment instrument according to the present embodiment is used; FIG. 2 is a schematic diagram illustrating an example of use of the bending treatment instrument according to the present embodiment; FIG. 3 is a side view illustrating a configuration of a forceps-equipped bending treatment instrument according to the present embodiment; FIGS. 4(a) to 4(c) are configuration diagrams each illustrating a configuration of a sheath and wire unit, where FIG. 4(a) is a configuration diagram illustrating a configuration of the sheath and wire unit, FIG. 4(b) is a diagram illustrating a variation of a bending wire and device wire, and FIG. 4(c) is a sectional view of the variation of the bending wire and device wire; FIG. 5 is a sectional view of an operating portion of the bending treatment instrument according to the present embodiment; FIG. 6 is a sectional view illustrating an internal structure of the operating portion; FIGS. 7 to 10 are exploded views illustrating a structure of a rotating device; FIG. 11 is a perspective view of a fixing base connecting portion; and FIG. 12 is a sectional view illustrating an internal structure of the fixing base connecting portion.

As shown in FIGS. 1 and 2, the bending treatment instrument according to the present embodiment includes a forceps-equipped bending treatment instrument 1a equipped with forceps at a distal end and a scalpel-equipped bending treatment instrument 1b equipped with an electric scalpel at a distal end. The bending treatment instruments 1a and 1b are inserted into an endoscope channel 2a of a flexible endoscope 2 or into a treatment instrument passage tube 2b attached to a distal end of the flexible endoscope 2, are inserted together with the flexible endoscope 2 through the mouth or anus of a patient 3, and are used to diagnose or resect an affected part 3a such as cancer in an abdominal cavity such as the digestive tract.

In so doing, the forceps-equipped bending treatment instrument 1a and scalpel-equipped bending treatment instrument 1b bend in a separate manner independently of the flexible endoscope 2 to provide at least two degrees of freedom, making it possible to grasp or resect the affected part 3a with a point of view of the flexible endoscope 2 fixed and carry out a procedure with a stable field of view and a high degree of freedom.

As shown in FIG. 3, the forceps-equipped bending treatment instrument 1a includes forceps 30 attached to a distal end of a bending portion 4 having two degrees of freedom in horizontal and vertical directions and openably and closably assembled using a device wire described later, an operating portion 60 used to perform bending motion of the bending portion 4 and open/close motion of the forceps 30, and a sheath and wire unit 5 equipped with plural wires adapted to transmit manipulation of the operating portion 60 and sheaths through which the wires are passed. Note that the scalpel-equipped bending treatment instrument 1b includes a bending portion and a sheath and wire unit as with the forceps-equipped bending treatment instrument 1a, and differs in being equipped with an electric scalpel at the distal end. The electric scalpel is constructed from an electrically conductive material and adapted to resect or cauterize an affected part by conducting a high-frequency current, and the distal end is formed, for example, into a spherical shape or hook shape. Also, an amount of protrusion of the distal end is configured to be adjustable appropriately by pushing and pulling a device wire 23 described later. Thus, regarding concrete description of the bending treatment instruments, the forceps-equipped bending treatment instrument 1a will be described, and detailed description of the scalpel-equipped bending treatment instrument 1b will be omitted.

As shown in FIG. 4, the sheath and wire unit 5 includes plural inner sheaths 21 through which plural bending wires 22 and a device wire 23 are passed, respectively, an outer sheath 24 through which the inner sheaths 21 are passed all together, a liner blade 25 covering an outer surface of the outer sheath 24, and a protective tube 26 covering an outer surface of the liner blade 25.

Each of the bending wires 22 is a stranded wire formed by twisting together plural stainless steel strands while the device wire 23 is a stranded wire formed by twisting together a smaller number of thicker stainless steel strands than the bending wire 22, and the bending wire 22 and device wire 23 have substantially the same outside diameter size. Specifically, the bending wire 22 is a stranded wire formed by twisting together nineteen stainless steel strands and preferably a stranded wire formed by twisting together seven stainless steel strands is used as the device wire 23. This configuration gives the bending wires 22 enough resilience to bend easily while giving the device wire 23 appropriate rigidity needed to open and close the forceps 30 and push and pull the electric scalpel.

Also, in relation to the bending wires 22 and device wire 23, as shown in FIGS. 4(*b*) and 4(*c*), each of a bending wire 22*a* and device wire 23*a* may be constructed by welding a swaging wire 28 to one end of a solid wire 27 of stainless steel. As shown in FIG. 4(*c*), the swaging wire 28 is formed by twisting together nineteen stainless steel strands and then swaging together the twisted strands by the application of pressure on an outer circumference. In this case, note that preferably surface treatment is applied to those portions of the outer circumferences of the solid wire 27 and swaging wire 28 that are inserted into the inner sheaths except for a distal side of the swaging wire 28 and a proximal side of the solid wire 27.

This configuration enables an arrangement in which the swaging wire 28 is passed through a portion corresponding to the bending portion 4 and the solid wire 27 is passed through a portion corresponding to the sheath and wire unit 5. Consequently, the passage of the solid wire 27 makes the sheath and wire unit 5 resistant to elongation and the bending portion 4 is provided with a structure having improved bendability. Note that since the swaging wire 28 has a structure in which the twisted strands are swaged together as described above, in welding the swaging wire 28 to the solid wire 27, it is possible to prevent filler metal from flowing out into space among the stranded wires due to capillary attraction and thereby improve weldability.

Also, the bending wires 22 and device wire 23 have been surface-treated to reduce sliding resistance in the inner sheaths 21. Note that preferably fluorocarbon resin, such as polytetrafluoroethylene, or fluorinated carbon resin is used for the surface treatment.

The inner sheaths 21, which guide push/pull motion of the bending wires 22 and device wire 23 and prevent the wires from interfering with each other, are so-called close-wound coils each formed by closely winding a flat metal wire with a flat cross section into a spiral. The use of flat wires makes it possible to ensure strength of the inner sheaths 21, increase an inside diameter size, and allows the bending wires 22 and device wire 23 passed through the inner sheaths 21 to perform push/pull motion smoothly. In contrast, if a round wire with a circular cross section is used for each of the inner sheaths 21, because adjoining turns of the round wire come into line contact with each other when the wire is wound into a spiral, if the inner sheaths 21 are bent when the bending treatment instruments are inserted into the endoscope channel or stored, position of the line contact moves in a circumferential direction, which poses a problem in that the round wires are buckled, causing shrinkage of the inner sheaths 21. Furthermore, as the wires are configured into close-wound coils, the inner sheaths 21 are configured not to be buckled or shrunk and stretched by the push/pull motion of the bending wires 22 and device wire 23. Also, regarding the inner sheaths 21, as shown in FIG. 4(*a*), the inner sheaths 21 through which the bending wires 22 are passed are arranged in the circumferential direction around the inner sheath 21 through which the device wire 23 is passed.

The outer sheath 24, which is a member making up a framework of the sheath and wire unit 5, protects the bending wires 22 and device wire 23 and transmits a turning force of the entire bending treatment instruments. As with the inner sheaths 21, the outer sheath 24 is formed by winding a flat metal wire with a flat cross section into a spiral, but is configured as a so-called coarse-wound coil having predetermined gaps. As the wire is configured into a coarse-wound coil in this way, resilience in a bending direction is improved and even if bent to a small radius, the sheath and wire unit 5 is not buckled and can bend smoothly by following the bending of the endoscope channel. Note that since the inner sheaths 21 themselves are prevented from shrinking by being wound closely as described above, even if the outer sheath 24 is wound coarsely, shrinkage of the sheath and wire unit 5 can be inhibited as much as possible.

When an external force acts on the bending portion 4 due to a load such as grasping motion of the forceps 30 or resection motion of the electric scalpel, the liner blade 25 prevents runout of an operating axis caused by the external force, and a mesh structure formed by cross-weaving metal wire strands is preferably used.

The protective tube 26 is a member adapted to cover and protect the sheath and wire unit 5 and electrically insulate a high-frequency high-voltage source applied to the electric scalpel. Specifically, it is preferable to use a heat-shrinkable tube made of polyolefin or the like.

As shown in FIG. 5, the operating portion 60 is attached to a fixing base connecting portion 62 via a linear-motion device 64 configured to be able to slide an operating portion body 63 in a longitudinal direction. By sliding the linear-motion device 64 along the longitudinal direction, the operating portion 60 allows the forceps 30, bending portion 4, and sheath and wire unit 5 to be pushed and pulled along the longitudinal direction and makes it possible to adjust an amount of protrusion of the forceps 30 from the endoscope channel 2*a* or treatment instrument passage tube 2*b*. Note that the fixing base connecting portion 62 includes a holding device 71 and an operating portion body fixing unit 72, and the operating portion body 63 is held in the longitudinal direction by the holding device 71 and operating portion body fixing unit 72.

As shown in FIG. 6, by making a grip 61 pivot up, down, left, and right like a joystick relative to the operating portion body 63, with the grip 61 being connected to the plural bending wires 22 passed through the sheath and wire unit 5, the operating portion 60 pushes and pulls the wires passed through the bending portion 4 and connected thereto in the longitudinal direction and thereby causes the bending portion 4 to perform bending motion. Also, the grip 61 includes a grip portion 67 and can perform push/pull motion on the grip portion 67 in the longitudinal direction and thereby pushes and pulls the device wire connected to the forceps 30 and electric scalpel, causing open/close motion of the forceps 30 and advance/retract operation of the electric scalpel.

The grip 61 includes a bending wire pulling unit 66 connected with the bending wires 22 and the grip portion 67 connected with the device wire 23. The bending wire pulling unit 66 includes a bending wire pulling unit body 66*a* formed into a spherical shape so as to be able to be connected with the plural bending wires 22 and able to operate the grip 61 like a joystick, and a spherical projection 81 formed substantially concentrically with the grip portion 67, extending in an axial direction from the bending wire pulling unit body 66a and projecting in a radial direction, with an outer surface of the spherical projection 81 being formed into a substantially spherical shape.

Also, the operating portion body 63 houses a guide unit 65, which is penetrated by the device wire 23. Also, a spherical recess 82 corresponding to the spherical projection 81 described above is formed on the guide unit 65, where the spherical projection 81 and spherical recess 82 are slidably engaged with each other, making up an axis alignment mechanism 80. The axis alignment mechanism 80 guides the bending wire pulling unit 66 pivotally up, down, left, and right with respect to the operating portion body 63. Also, when the device wire 23 bends along with pivoting of the bending wire pulling unit 66, the axis alignment mechanism 80 facilitates the push/pull motion of the device wire 23 by axially aligning the device wire 23 and the sheath and wire unit 5 with each other at the position of the axis alignment mechanism 80.

A rotating device 90 adapted to rotatably assemble the operating portion body 63 onto the fixing base connecting portion 62 is attached to the operating portion body 63, and a fixing unit 91 fitted over a fixing unit holder 74 formed on the fixing base connecting portion 62 is attached to the rotating device 90. Being continuous with the sheath and wire unit 5, the fixing unit 91 passes components of the sheath and wire unit 5 including the bending wires 22, device wire 23, inner sheaths 21, and outer sheath 24 therethrough.

As shown in FIGS. 7 to 10, the rotating device 90 includes a wire holder 92 through which the bending wires 22, device wire 23, and inner sheaths 21 are passed; a rotating portion 93 rotatably assembled onto the fixing unit 91; and a rotation controller 94 onto which the rotating portion 93 is assembled.

The wire holder 92 is fixed and stored in the fixing unit 91. Also, the wire holder 92 is provided with holes through which the inner sheaths 21 are passed one by one without being entangled, the inner sheaths 21 project into the operating portion body 63 from ends of the holes, and the plural bending wires 22 passed through the inner sheaths 21 spread inside the rotating portion 93, spanning across the bending wire pulling unit 66.

Figure 9:
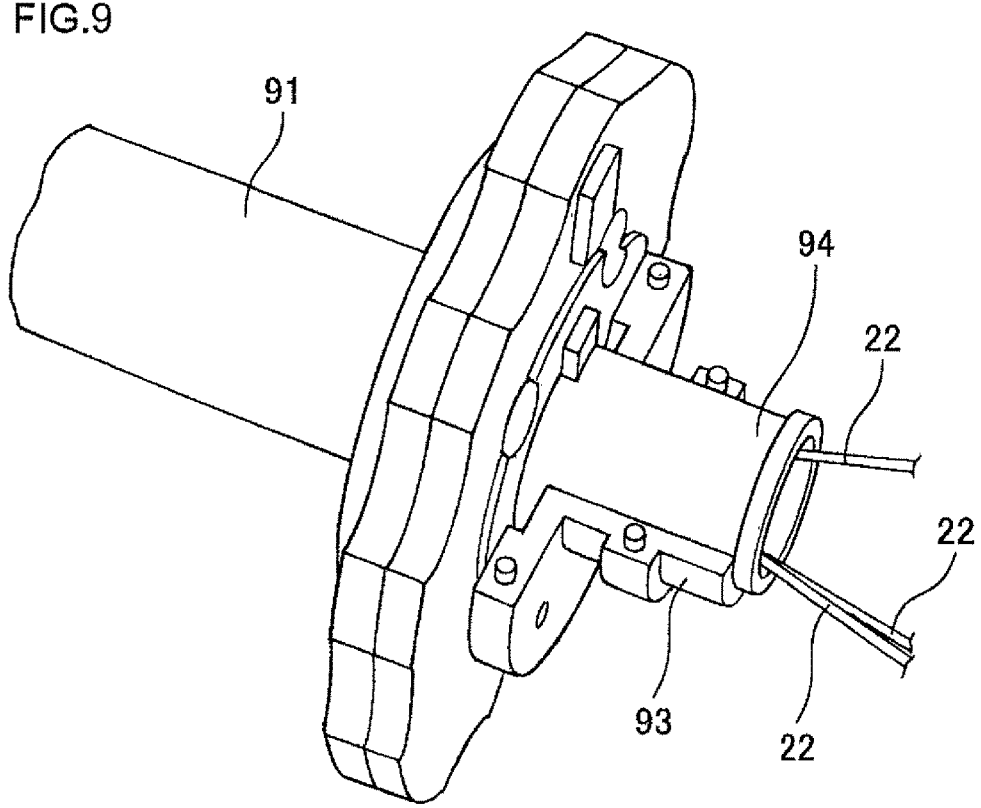
FIG. 9 is an exploded view illustrating a structure of the rotating device.
Figure 10:
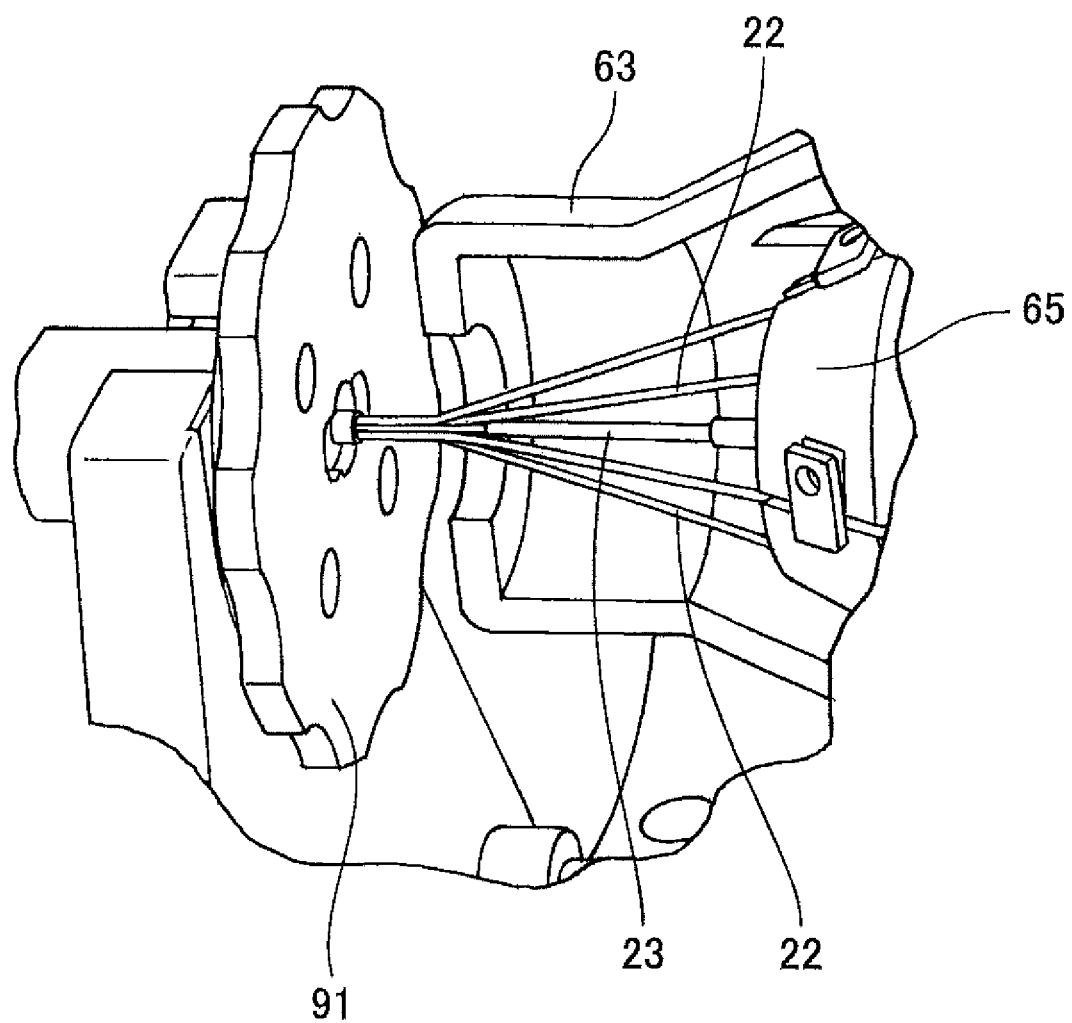
FIG. 10 is an exploded view illustrating a structure of the rotating device.

As shown in FIG. 9, the rotating portion 93 is slidably assembled onto the rotation controller 94 at one end and assembled at another end in such a way as to be fixed to the operating portion body 63. Together with the operating portion body 63, the rotating portion 93 is assembled axially rotatably on the fixing unit 91 assembled integrally with the rotation controller 94. Also, if a stopper is formed on the rotation controller 94 to restrict rotation of the rotating portion 93, making up a mechanism whereby the rotation is stopped by the stopper when the rotating portion 93 rotates a predetermined angle, the mechanism can keep the operating portion body 63 from rotating more than necessary. Consequently, the mechanism allows the operating portion body 63 to rotate relative to the fixing unit 91 while further serving as a rotation control mechanism adapted to keep the operating portion body 63 from rotating more than a predetermined amount.

In this way, since the bending treatment instrument according to the present embodiment is equipped with the rotating device 90 between the fixing unit 91 and operating portion body 63, allowing the operating portion body 63 to rotate relative to the fixing base connecting portion 62, if a discrepancy occurs between a bending direction of the bending portion 4 and an input direction of the operating portion 60 due to twisting caused when the bending treatment instrument is inserted into the endoscope channel, the input direction of the operating portion 60 and the bending direction of the bending portion 4 can be brought into coincidence with each other, making it possible to implement intuitive operation.

Also, since the operating portion body 63 is attached to the rotating device 90 via the rotating portion 93, a space can be provided between the fixing unit 91 and operating portion body 63, and if predetermined slack is given to the bending wires 22 in the space, friction among the bending wires 22 can be reduced, making it possible to rotate the operating portion body 63 smoothly. Specifically, an appropriate space can be provided between the rotating device 90 and an end of the guide unit 65, and more specifically, between a proximal side end portion of the wire holder 92 and contact points of the guide unit 65 with the bending wires 22. For example, preferably a spatial distance between the proximal side end portion of the wire holder 92 and the contact points of the guide unit 65 with the bending wires 22 is 10 mm or above, more preferably 15 mm or above, still more preferably 20 mm or above, and most preferably 30 mm or above.

Furthermore, since the inner sheaths 21 are extended from the wire holder 92 so as to project into the operating portion body 63, friction among the bending wires 22 can be reduced at an end of the wire holder 92 where the bending wires 22 are located close to one another, which makes it possible to rotate the operating portion body 63 smoothly. Also, it is enough that the inner sheaths 21 extend into the operating portion body 63, and, for example, to prevent the bending wires 22 from entangling with one another, it is enough that the inner sheaths 21 extend to a location where the bending wires 22 are located close to one another, and more preferably, it is preferable to extend tips of the inner sheaths 21 to contact points of the guide unit 65 with the bending wires 22. Specifically, it is more preferable to fix the tips of the inner sheaths 21 by bonding to the guide unit 65 or via a mounting member.

Next, the fixing base connecting portion 62 will be described with reference to FIGS. 11 and 12.

The fixing base connecting portion 62 includes the holding device 71, the operating portion body fixing unit 72 movable toward and away from the holding device 71 in the longitudinal direction, and the fixing unit holder 74 adapted to fix the fixing unit 91 by getting engaged with the fixing unit 91. The operating portion body fixing unit 72 can hold the operating portion body 63 between the holding device 71 and the operating portion body fixing unit 72 in the longitudinal direction by getting engaged with a tail end of the operating portion body 63 and moving toward the operating portion body 63 in the longitudinal direction.

This configuration makes it possible to detachably assemble the bending treatment instrument easily onto the fixing base connecting portion 62. Note that rotating operation of the operating portion body 63 can be performed suitably with the operating portion body 63 unheld by spacing the operating portion body fixing unit 72 away from the holding device 71.

Note that the operating portion body fixing unit 72 is operated linearly by a rotation lock 73, which is meshed with a rack 75 formed in the operating portion body fixing unit 72 as shown in FIG. 12. With this configuration, when the rotation lock 73 is rotated, the rack 75 meshed with the rotation lock 73 moves along the longitudinal direction, thereby making the operating portion body fixing unit 72 movable toward and away from the holding device 71.

Also, the holding device 71 and operating portion body fixing unit 72 are attached to a mount 78 by the linear-motion device 64. By being assembled to a fixing base 70, the mount 78 fixes a position of the bending treatment instrument during surgery.

The linear-motion device 64 is made up of a linear-motion plate 76 on which the holding device 71 and operating portion body fixing unit 72 are assembled together, and a guide 77 adapted to guide the linear-motion plate 76 along the longitudinal direction, in which as the linear-motion plate 76 moves along the longitudinal direction, the operating portion body 63 held by the holding device 71 can be moved along the longitudinal direction and the bending treatment instrument can be moved in an insertion direction of the bending treatment instrument relative to the endoscope channel or treatment instrument passage tube.

In this way, with the bending treatment instrument according to the present embodiment, even if outside diameters of the bending portion 4 and the sheath and wire unit 5 are minimized to 3.8 mm or below to allow the bending portion 4 and the sheath and wire unit 5 to be passed through the endoscope channel, when the bending portion 4 performs bending motion in the operating portion body 63, the bending motion is not obstructed by interference of a hinge member 10 with the bending wires 22 or device wire 23 passed through the bending portion 4 and the push/pull motion of the bending wires 22 and device wire 23 produced by manipulation of the operating portion 60 can be transmitted reliably to the bending portion 4 as well as to the forceps 30 or an electric scalpel 36.

Also, even if the outside diameter of the sheath and wire unit 5 is minimized, when the sheath and wire unit 5 passes, for example, the bending treatment instrument through the endoscope channel or if twisting is caused in the endoscope channel by operation of the endoscope or the like, the operating axis can be adjusted through rotation of the operating portion body 63, enabling more intuitive operation.

Second Embodiment

In the bending treatment instrument according to the first embodiment described above, the operating portion body is attached rotatably and detachably to the fixing base via the fixing base connecting portion. A bending treatment instrument according to a second embodiment described next is an example having a form different from the first embodiment. Note that components identical or similar to those of the first embodiment described above are denoted by the same reference numerals as the corresponding components of the first embodiment, and description thereof will be omitted.

Figure 13:
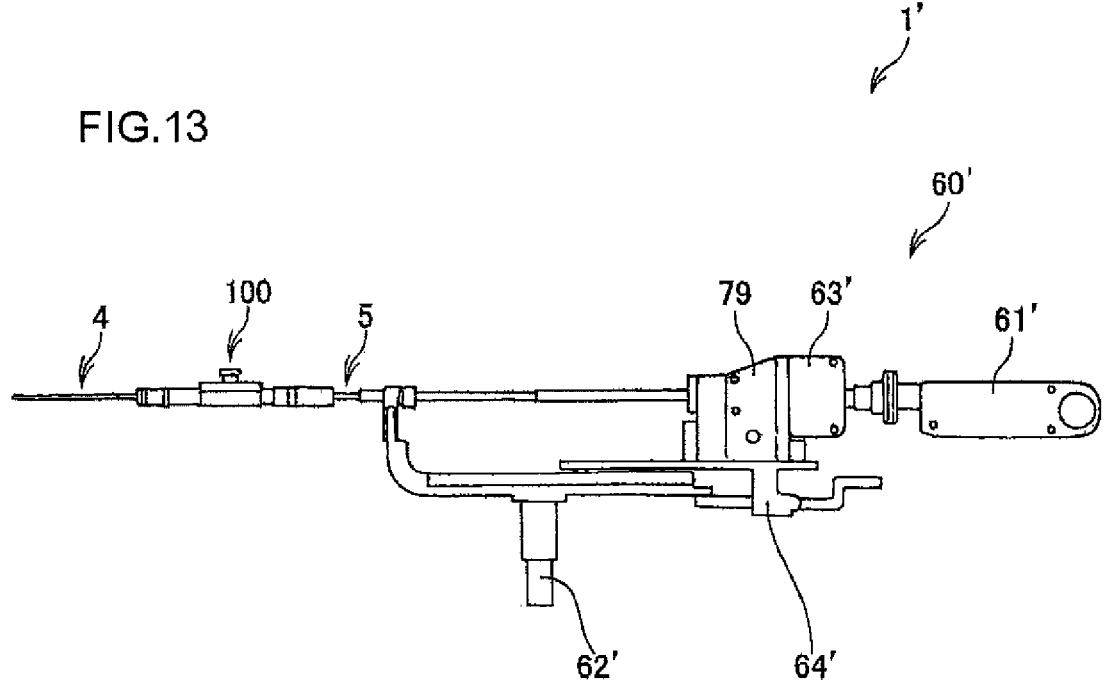
FIG. 13 is a side view of an operating portion of a bending treatment instrument according to a second embodiment.
Figure 14:
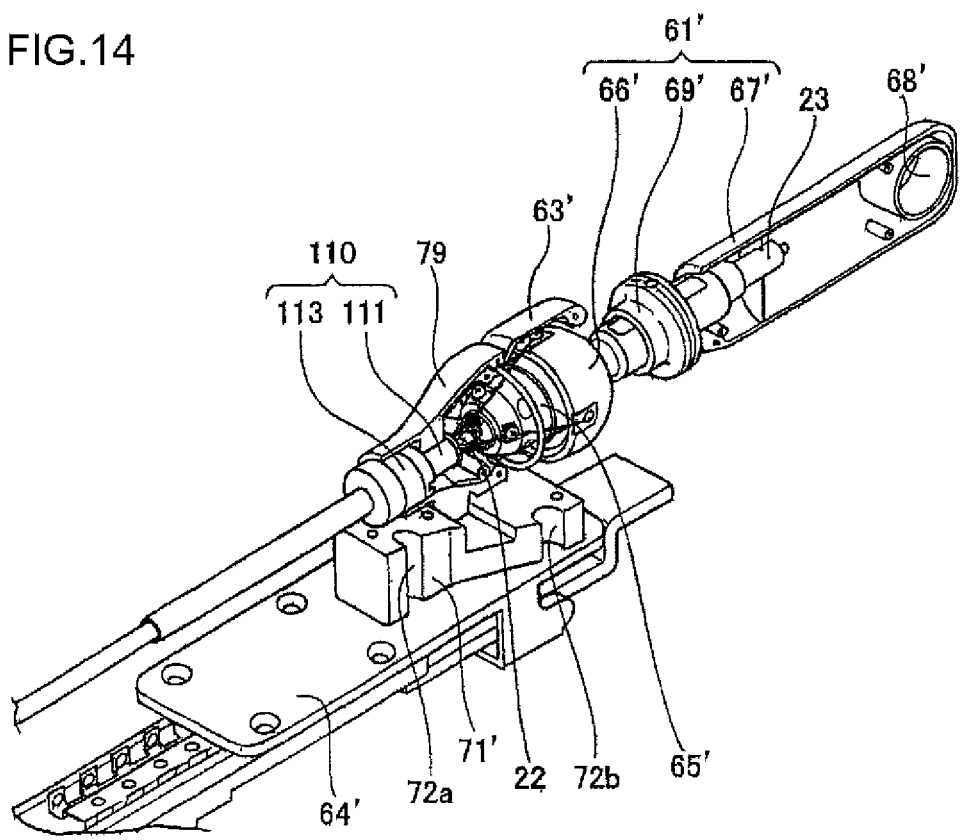
FIG. 14 is an exploded view illustrating an internal structure of the operating portion.
Figure 15:
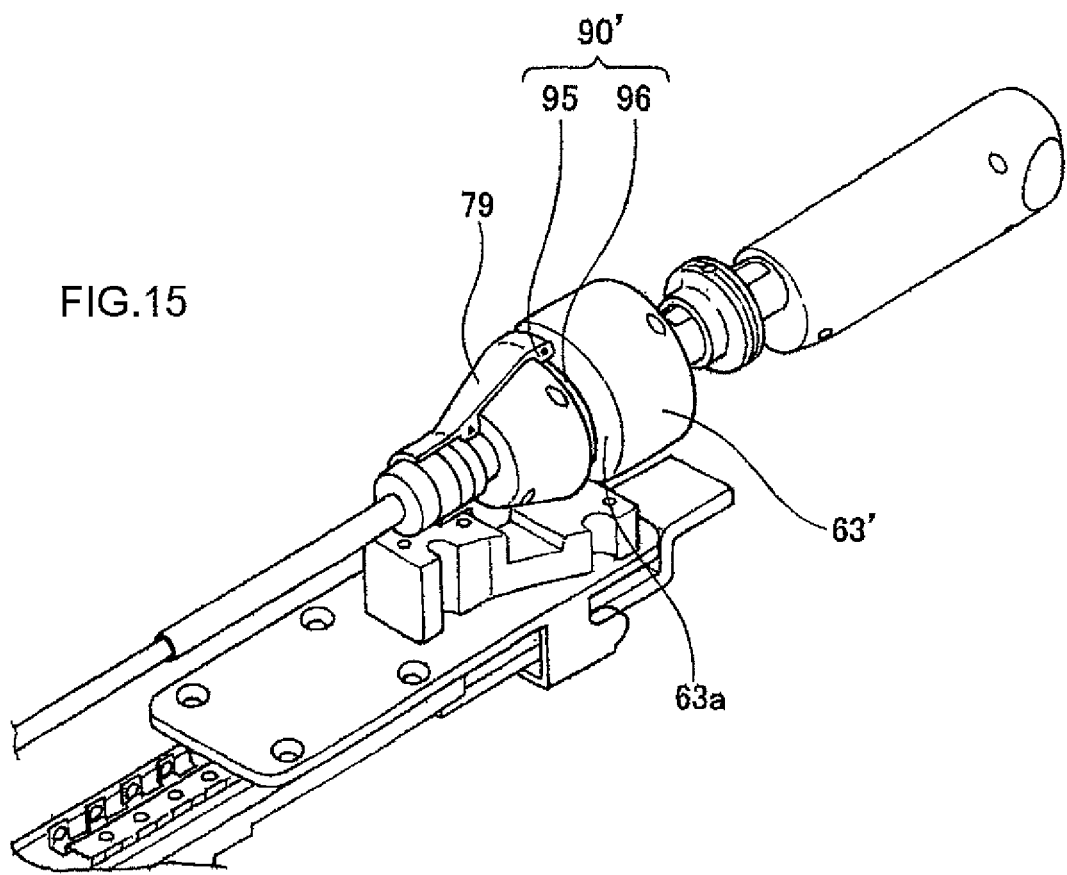
FIG. 15 is an exploded view illustrating a structure of a rotating device.
Figure 16:
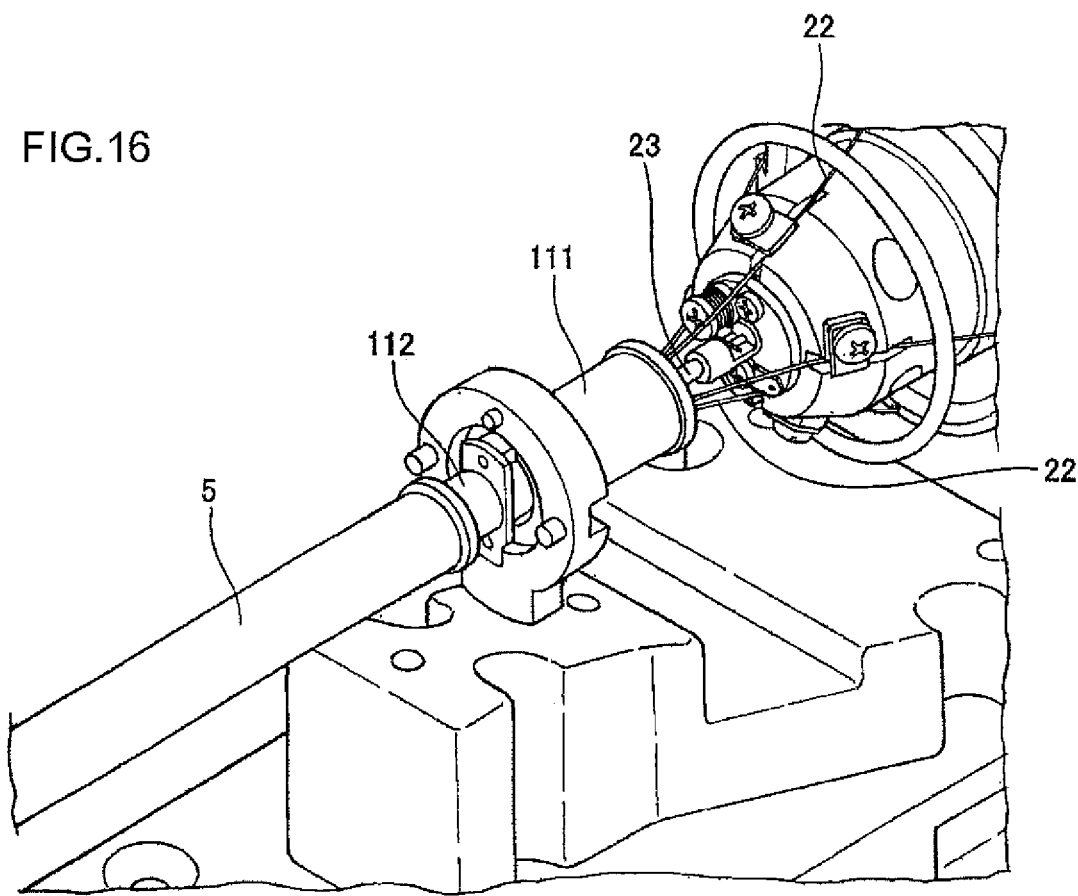
FIG. 16 is an exploded view illustrating a structure of a twisting force relief mechanism.
Figure 17:
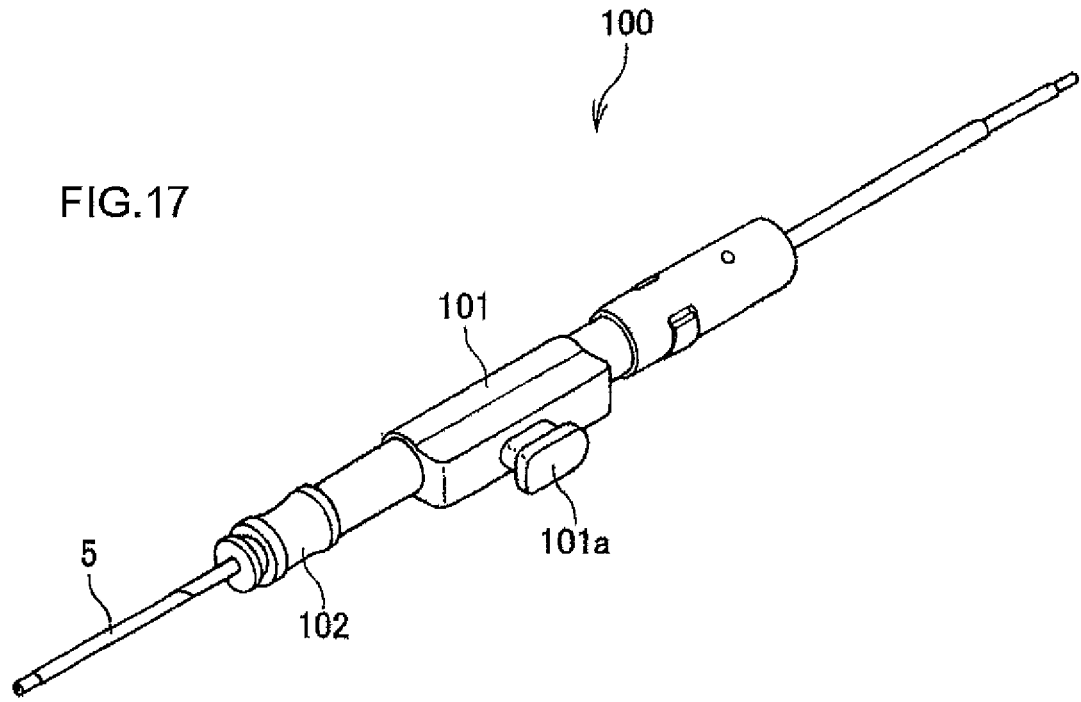
FIG. 17 is a perspective view of an axial fixing unit.
Figure 18:
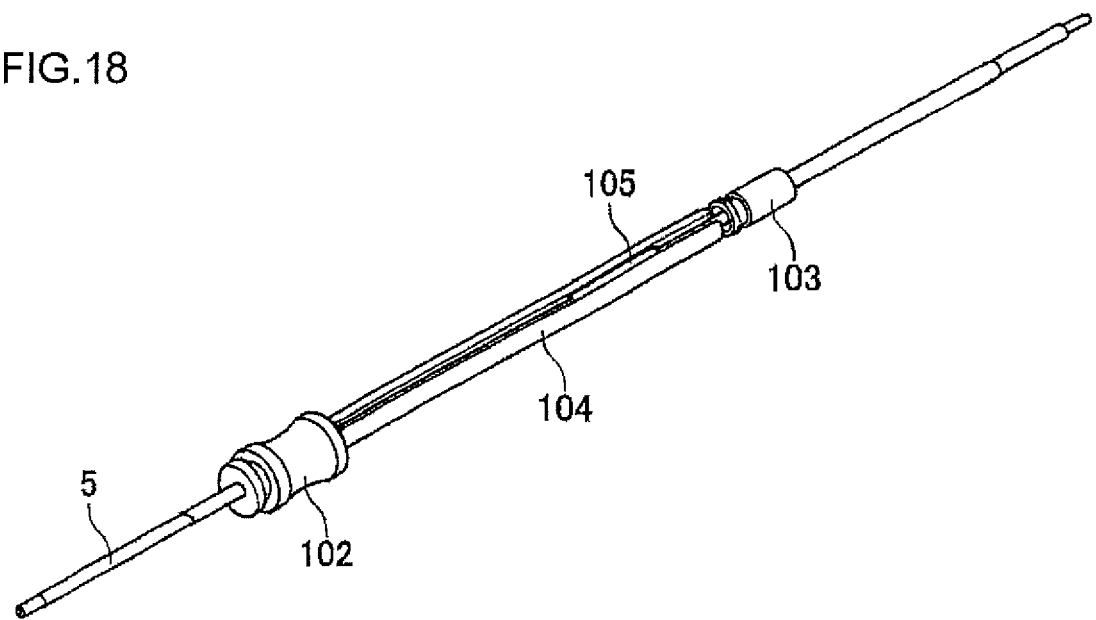
FIG. 18 is an exploded view illustrating a structure of the axial fixing unit.

FIG. 13 is a side view of an operating portion of a bending treatment instrument according to the second embodiment; FIG. 14 is an exploded view illustrating an internal structure of the operating portion; FIG. 15 is an exploded view illustrating a structure of a rotating device; FIG. 16 is an exploded view illustrating a structure of a twisting force relief mechanism; FIG. 17 is a perspective view of an axial fixing unit; and FIG. 18 is an exploded view illustrating a structure of the axial fixing unit.

As shown in FIGS. 13 and 14, a bending treatment instrument 1' according to the present embodiment includes forceps or an electric scalpel (neither is shown) attached to a distal end of a bending portion 4 having two degrees of freedom in horizontal and vertical directions and openably and closably assembled using a device wire 23 described later, an operating portion 60' used to perform bending motion of the bending portion 4 and open/close motion of the forceps or advance/retract motion of the electric scalpel, and a sheath and wire unit 5 equipped with plural bending wires 22 adapted to transmit manipulation of the operating portion 60' and sheaths through which the wires are passed. Also, an axial fixing device 100 is attached to the sheath and wire unit 5.

The operating portion 60' is attached to a fixing base connecting portion 62' via a linear-motion device 64' configured to be able to slide an operating portion body 63' in a longitudinal direction. By sliding the linear-motion device 64' along the longitudinal direction, the operating portion 60' allows the bending portion 4 and the sheath and wire unit 5 to be pushed and pulled along the longitudinal direction and makes it possible to adjust an amount of protrusion of the forceps or electric scalpel attached to the distal end of the bending portion from the endoscope channel 2a or treatment instrument passage tube 2b.

The fixing base connecting portion 62' includes a holding device 71'. A first anchoring portion 72a and a second anchoring portion 72b both shaped like a groove are formed on the holding device 71', extending at right angles to the longitudinal direction. The first anchoring portion 72a is formed so as to be higher than the second anchoring portion 72b.

Also, a twisting force relief mechanism 110 is attached to the operating portion body 63' on the distal side and a cover body 79 is attached covering the twisting force relief mechanism 110. By being press-fitted into the first anchoring portion 72a and second anchoring portion 72b formed on the holding device 71' from the vertical direction along an extending direction of the first anchoring portion 72a and second anchoring portion 72b, the cover body 79 can be anchored to the fixing base connecting portion 62', thereby holding the operating portion body 63' in the longitudinal direction. Note that the first anchoring portion 72a is formed so as to be longer than the second anchoring portion 72b, making it easy to attach and detach the operating portion body 63' by reducing frictional force with respect to the second anchoring portion 72b.

By making a grip 61' pivot up, down, left, and right like a joystick relative to the operating portion body 63' with the grip 61' being connected to the plural bending wires 22 passed through the sheath and wire unit 5, the operating portion 60' pushes and pulls the wires passed through the bending portion 4 and connected thereto in the longitudinal direction and thereby causes the bending portion 4 to perform bending motion.

Also, the grip 61' includes an operating mobile body 69' and can perform push/pull motion on the operating mobile body 69' in the longitudinal direction and thereby pushes and pulls the device wire 23 connected to the forceps and electric scalpel, causing open/close motion of the forceps and advance/retract operation of the electric scalpel.

The grip 61' includes a bending wire pulling unit 66' connected with the bending wires 22 and the grip portion 67' connected with the device wire 23. Also, the operating portion body 63' houses a guide unit 65', which is penetrated by the device wire 23. Furthermore, a finger ring portion 68' annular in shape is formed at a tip of the grip 61' to facilitate up, down, left, and right pivoting operation of the bending wire pulling unit 66' and reciprocating motion of the grip portion 67'.

As shown in FIG. 15, the operating portion body 63' is assembled on the cover body 79 via a rotating device 90' adapted to rotatably assemble the operating portion body 63' onto the fixing base connecting portion 62'. The rotating device 90' includes a restraining member 96 made of elastic material such as rubber and provided in a rotating groove 63a formed in a circumferential direction of the operating portion body 63' and a rotating protrusion 95 formed in the cover body 79 by corresponding to the rotating groove 63a and restrains relative rotation between the operating portion body 63' and cover body 79 by means of a frictional force generated when the rotating protrusion 95 is pressed against the restraining member 96. Note that the cover body 79 and operating portion body 63' restrain each other only by means of the frictional force, and thus by imparting a turning force tending to rotate the operating portion body 63' in the circumferential direction, the operating portion body 63' can be rotated relatively easily, making it possible to bring the bending direction of the bending portion 4 and an operating direction of the grip 61' into coincidence and thereby improve operability.

Because the bending treatment instrument 1' according to the present embodiment can fix the axial fixing device 100 attached to the sheath and wire unit 5 to an endoscope holder provided on the endoscope, by fixing an insertion posture of the bending treatment instrument 1', the bending treatment instrument 1' is configured to inhibit rotation of the bending portion 4 and the sheath and wire unit 5 in the endoscope channel 2a and treatment instrument passage tube 2b and thereby eliminate the need for an axis alignment operation of bringing the operating direction of the grip 61' and the bending direction of the bending portion 4 into coincidence.

However, with this configuration, if a superfluous twist force is produced on the sheath and wire unit 5 or the like while the operating portion 60' is being handled, a load is applied to the axial fixing device 100, and conceivably the axial fixing device 100 will fall off the endoscope holder or other similar problems will arise. To prevent this, the twisting force relief mechanism 110 is attached to the operating portion 60' to scatter any twist force produced on the sheath and wire unit 5.

As shown in FIG. 16, the twisting force relief mechanism 110 includes a twisting force relief mechanism body 111 through which the bending wires 22 and device wire 23 are passed, the bending wires 22 and device wire 23 also being passed through the sheath and wire unit 5, and a rotating body 112 assembled axially rotatably in a circumferential direction on the twisting force relief mechanism body 111. The rotating body 112 is anchored to an end portion of the sheath and wire unit 5, and pinched by the twisting force relief mechanism body 111 and a covering member 113 as shown in FIG. 14, and thus the rotating body 112 is held immovably in a passage direction of the device wire 23 and bending wires 22.

With the twisting force relief mechanism 110 which is configured in this way, even if twisting forces are produced on the operating portion 60' and the sheath and wire unit 5 while the operating portion 60' is being handled, the rotating body 112 rotates according to the twisting forces, thereby scatters the twisting forces, and prevents application of loads to the axial fixing device 100.

Next, the axial fixing device 100 will be described with reference to FIGS. 17 and 18. As shown in FIG. 17, the axial fixing device 100 includes an axial fixing device body 101 through which the sheath and wire unit 5 is passed, and a distal restrainer 102 mounted on a distal side of the axial fixing device body 101. A holder fixing unit 101a fixed to the endoscope holder is formed, on the axial fixing device body 101 and by fixing the holder fixing unit 101a to the endoscope holder, the insertion posture of the bending treatment instrument 1' can be fixed.

As shown in FIG. 18, the axial fixing device body 101 contains an axial fixing unit 104 in which a groove is formed along the longitudinal direction. When fitted in the groove, an engaging protrusion 105 attached to an outer circumference of the sheath and wire unit 5 prevents rotation of the sheath and wire unit 5 in the circumferential direction while allowing the sheath and wire unit 5 to slide in the longitudinal direction. Note that the distal restrainer 102 and a proximal restrainer 103 are attached to opposite ends of the axial fixing unit 104 in the longitudinal direction and that by abutting the distal restrainer 102 and proximal restrainer 103, the engaging protrusion 105 is restricted from sliding in the longitudinal direction and thereby prevented from falling off the groove in the axial fixing unit 104.

Whereas preferred embodiments of the present invention has been described above, the technical scope of the present invention is not limited to the description of the above embodiments. Various changes or improvements can be made to the above embodiment.

In relation to the bending treatment instrument according to the present embodiment, description has been given of a case in which the forceps-equipped bending treatment instrument 1a and scalpel-equipped bending treatment instrument 1b are used at the same time by being inserted into the endoscope channel 2a and treatment instrument passage tube 2b, respectively, but only one of the forceps-equipped bending treatment instrument 1a and scalpel-equipped bending treatment instrument 1b may be used. Alternatively, for example, a clip-equipped bending treatment instrument, exclusion bending treatment instrument, or needle-carrier bending treatment instrument may be used other than the forceps-equipped bending treatment instrument 1a and scalpel-equipped bending treatment instrument 1b. Also, description has been given of a case in which the operating portion of the bending treatment instrument according to the present embodiment is equipped with the axis alignment mechanism 80 in which the spherical projection 81 is formed on the bending wire pulling unit 66 and the spherical recess 82 is formed in the guide unit 65, but the projection and recess may be formed the other way around.

It will be apparent from the description in the appended claims that any form resulting from such changes or improvements is also included in the technical scope of the present invention.

REFERENCE SIGNS LIST

1a Forceps-equipped bending treatment instrument
1b Scalpel-equipped bending treatment instrument
1' Bending treatment instrument
2 Flexible endoscope
2a Endoscope channel
2b Treatment instrument passage tube
3 Patient
3a Affected part
4 Bending portion
5 Sheath and wire unit
21 Inner sheath
22 Bending wire
23 Device wire
24 Outer sheath
25 Liner blade
26 Protective tube 30 Forceps
60, 60' Operating portion
61, 61' Grip
62, 62' Fixing base connecting portion
63, 63' Operating portion body
64, 64' Linear-motion device
65, 65' Guide unit
66, 66' Bending wire pulling unit
67, 67' Grip portion
68, 68' Finger ring portion
70 Fixing base
71, 71' Holding device
72 Operating portion body fixing unit
72a First anchoring portion
72b Second anchoring portion
73 Rotation lock
74 Fixing unit holder
75 Rack
76 Linear-motion plate
77 Guide
78 Mount
79 Cover body
80 Axis alignment mechanism
81 Spherical projection
82 Spherical recess
90, 90' Rotating device
91 Fixing unit
92 Wire holder
93 Rotating portion
94 Rotation controller
95 Rotating protrusion
96 Restraining member
100 Axial fixing device
101 Axial fixing device body
101a Holder fixing unit
102 Distal restrainer
103 Proximal restrainer
104 Axial fixing unit
105 Engaging protrusion
110 Twisting force relief mechanism
111 Twisting force relief mechanism body
112 Rotating body
113 Covering member

The invention claimed is:

1. An operating portion connected with a device wire and a plurality of bending wires and used to operate a treatment instrument and bend a freely bendable, bending treatment instrument, the device wire being connected to the treatment instrument provided at a distal end of the bending treatment instrument and used to operate the treatment instrument and the plurality of bending wires being used to bend the bending treatment instrument, the operating portion comprising:
   an operating portion body;
   a guide unit penetrated by the device wire;
   a bending wire pulling unit connected with the bending wires and swingably assembled onto the guide unit; and
   a grip portion connected with the device wire and configured to be reciprocable in an axial direction of the bending wire pulling unit,
   wherein the operating portion body is detachably attached to a fixing base via a fixing base connecting portion,
   wherein a rotating device adapted to rotatably assemble the operating portion body onto the fixing base connecting portion is attached to the operating portion body, and the rotating device includes a fixing unit fixed to the fixing base connecting portion, a rotating portion rotatably assembled onto the fixing unit, and a rotation controller onto which the rotating portion is assembled, and
   wherein the bending wires are provided through the fixing unit, the rotating portion, and the rotation controller of the rotating device.

2. The operating portion according to claim 1, wherein the bending wire pulling unit and the guide unit include an axis alignment mechanism made up of a spherical recess and a spherical projection fitted one inside another, the spherical recess being formed in one of the bending wire pulling unit and the guide unit, and the spherical projection being formed on another of the bending wire pulling unit and the guide unit.

3. The operating portion according to claim 1, wherein the fixing base connecting portion includes a holding device adapted to hold the operating portion body in a longitudinal direction.

4. The operating portion according to claim 1, wherein the fixing base connecting portion includes a linear-motion device adapted to guide the operating portion body in an extending direction of the device wire.

5. The operating portion according to claim 1, wherein the operating portion body includes a twisting force relief mechanism, that comprises at least one body, adapted to prevent twisting of the device wire and the bending wires in a circumferential direction.

6. The operating portion according to claim 5, wherein the at least one body of the twisting force relief mechanism includes: a twisting force relief mechanism body adapted to allow passage of the device wire and the bending wires; and a rotating body assembled immovably relative to the twisting force relief mechanism body in a passage direction of the device wire and the bending wires and turnably in the circumferential direction.

7. The operating portion according to claim 1, wherein the fixing base connecting portion includes a holding device adapted to anchor, through press-fitting, a cover body attached to the operating portion body.

8. The operating portion according to claim 7, wherein the holding device includes a first anchoring portion and a second anchoring portion both shaped like a groove and configured to extend substantially at right angles to a longitudinal direction.

* * * * *